Figure 1:
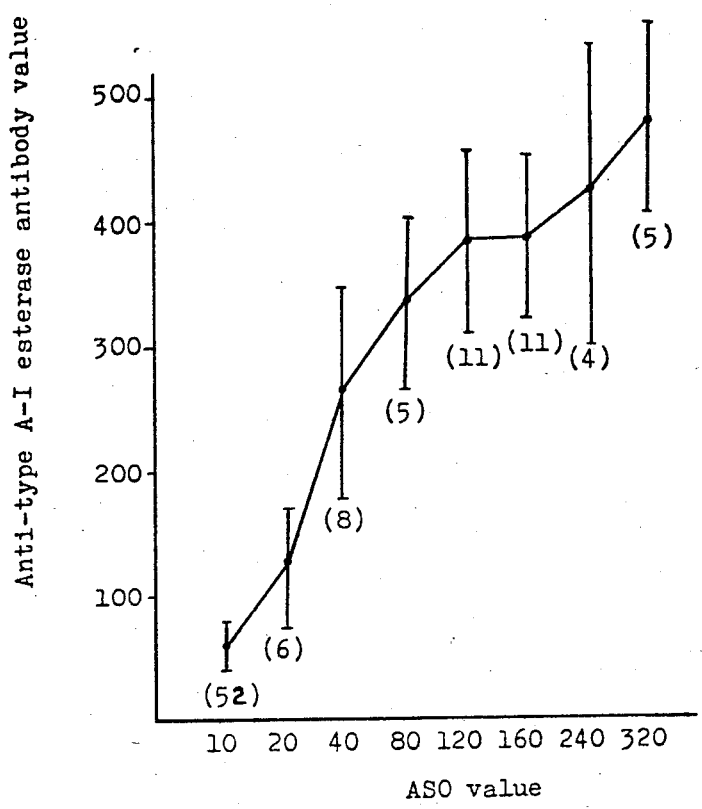

United States Patent [19]

Hayano et al.

[11] Patent Number: 4,592,995

[45] Date of Patent: Jun. 3, 1986

[54] REAGENT FOR STREPTOCOCCAL ANTI-ESTERASE ASSAY

[75] Inventors: Seiki Hayano, Omiya; Kanae Yokogawa, Nara; Shigeru Kurooka, Fujiidera, all of Japan

[73] Assignee: Dainippon Pharmaceutical Co., Ltd., Osaka, Japan

[21] Appl. No.: 552,014

[22] Filed: Nov. 16, 1983

Related U.S. Application Data

[63] Continuation of Ser. No. 249,231, Mar. 30, 1981, abandoned.

[51] Int. Cl.[4] .............. G01N 33/573; G01N 33/569; G01N 33/554; G01N 33/548; G01N 33/552
[52] U.S. Cl. .................................. 435/7; 435/810; 436/519; 436/527; 436/529; 436/828
[58] Field of Search ............... 435/4, 7, 19, 34, 36, 435/810, 885, 39; 436/828, 519, 527, 529

[56] References Cited

U.S. PATENT DOCUMENTS

| | | | |
|---|---|---|---|
| 3,790,447 | 4/1974 | Hiratla et al. | 435/7 |
| 3,791,932 | 2/1974 | Schuurs et al. | 435/7 |
| 3,932,221 | 1/1976 | Pfleider | 435/19 |
| 4,012,285 | 3/1977 | Pfleider et al. | 435/4 |
| 4,016,043 | 4/1977 | Schuurs et al. | 435/7 |
| 4,166,767 | 9/1979 | Kurooka et al. | 435/885 |
| 4,366,242 | 12/1982 | Neumann et al. | 435/7 |

OTHER PUBLICATIONS

Dainippon Pharmaceutical Co., "Reagents for Antibody Determination", Chem. Absts., vol. 95, No. 7, (1981) Absts. #57653f.
Soudon et al., "A New Rapid and Reliable Test for the Demonstration of Streptococcal Anti-Exoenzyme Antibodies", Chem. Absts., vol. 86, No. 17 (1977) p. 368, Absts. No. 119048n.
Hayano et al., "Repetitive Counterelectrophoresis on Agar Gel for the Immunological Identification of Esterases Produced by Strains of Lance Field's Group A B and C Streptococci", Infection and Immunology, vol. 15, No. 1, (1977), pp. 295–299.
Forsgren et al., "Protein A from S. Aureus", J. Immunol, vol. 97, No. 6 (1966), pp. 822–827.
Frohman et al., "Use of Protein A-Containing Streptococcus Aureus as an Immuno Adsorbent in Radio Immunoassays to Separate Antibody-Bound from Free Antigen", J. Lab. Clin. Med., vol. 93, No. 4 (1979), pp. 614–620.
Shigeyo Shibazaki et al.; J. Clin. Lab. Inst. Reag., 6(4), 1037–1043 (1983) Abstract.
Seiichi Kawakita et al.; Clin. Report, 17(9), 2994–3002 (1983) Abstract.
Kunio Nakajima et al.; J. Pediatric Practice, 46(9), 1419–1438 (1983) Abstract.
Yukiyoshi Nakamura et al.; J. Jap. Assoc. Infect. Dis., 57(9), 771–775 (1983) Abstract.

Primary Examiner—Esther M. Kepplinger
Attorney, Agent, or Firm—Stevens, Davis, Miller & Mosher

[57] ABSTRACT

A reagent for the determination of an antibody against an esterase from pathogenic streptococci, which comprises reagent 1: an esterase (a) from pathogenic streptococci,
reagent 2: a protein (b) which is capable of binding to an antibody (d) against the esterase (a) and is bound to an insoluble carrier, and
reagent 3: a reagent (c) for measuring an activity of the esterase (a), and a method for the determination of an antibody against an esterase from pathogenic streptococci. The reagent and method of the present invention are useful for diagnosis of various diseases caused by pathogenic streptococcal infections.

7 Claims, 1 Drawing Figure

Figure in the parenthesis is number of patients.

Mark • means the average.

REAGENT FOR STREPTOCOCCAL ANTI-ESTERASE ASSAY

This application is a continuation of application Ser. No. 249,231, filed Mar. 30, 1981, now abandoned.

The present invention relates to a reagent for a streptococcal anti-esterase assay. More particularly, it relates to a novel reagent useful for the determination of an anti-esterase antibody, i.e. an antibody against an esterase from pathogenic streptococci.

In serodiagnosis of diseases caused by pathogenic streptococcal infections such as rheumatic fever, acute glomerulonephritis and scarlet fever particularly in those diseases caused by infections of Lancefield's hemolytic group A streptococci, it has, hitherto, been done by determining the titer of an antibody against extracellar components. There have usually been determined the antibody against Streptolysin O (ASO) and the antibody against deoxyribonuclease B. Antibody against hyaluronidase, streptokinase or NAD nucleotidase is occasionally determined.

It has been also reported by Hayano to determine an anti-esterase antibody [cf. Seiki Hayano, Infection and Immunity 15 (1), 295-299 (1977)]. According to this method, the anti-esterase antibody and the esterase (antigen) are spotted on an agar gel plate and subjected to a repetitive counter electrophoresis and then the esterase bound to the anti-esterase antibody on the agar gel plate is colored by spraying chromogenic substrate reagent, and the resulting appeared moved spot is measured. The value of anti-esterase antibody is determined based on the size of the colored spot. This method is advantageous in that it can be done even with a small amount of test materials and that the gel plate with colored spots can be kept for a long period of time. However, it has such disadvantages as requiring complicated procedures and being time consuming (about 48 hours), and further, the obtained data are not quantitative (rather qualitative) because they are determined from the size of spot.

The present inventors have intensively studied improvement of the determination of an antibody against an esterase from pathogenic streptococci in human blood serum. As a result, it has been found that the anti-esterase antibody can quantitatively be determined within a very short period of time such as about one to two hours with a small amount of a test material by the method comprising adding an esterase obtained from a culture broth of a pathogenic streptococcus and a human blood serum into a test tube, adding thereto an insoluble protein being capable of binding to human immunoglobulin, incubating the mixture, separating the resulting "an esterase-anti-esterase antibody-insoluble protein" complex, and then determining the esterase activity thereof with a conventional reagent for determining esterase activity, wherein the esterase activity is in a quantitative relation with the amount of the anti-esterase antibody in the human blood serum.

An object of the present invention is to provide a reagent useful for the improved method for the determination of an antibody against an esterase from pathogenic streptococci, i.e. for streptococcal anti-esterase assay. Another object of the invention is to provide an improved method for the determination of the anti-esterase antibody which is useful for serodiagnosis of diseases caused by pathogenic streptococcal infections. These and other objects and advantages of the invention will be apparent to persons skilled in the art from the following description.

The reagent for streptococcal anti-esterase assay of the present invention comprises a kit of the following reagents:

reagent 1: an esterase (a) from pathogenic streptococci, reagent 2: a protein (b) which is capable of binding to an antibody (d) against the esterase (a) from pathogenic streptococci and is bound to an insoluble carrier, and reagent 3: a reagent (c) for measuring an activity of the esterase (a).

The esterase (a) (reagent 1, which may occasionally be referred to as "antigen") can be obtained by cultivating a pathogenic streptococcus, fractionating the resulting culture broth containing esterase with ammonium sulfate, subjecting the resulting fraction to dialysis and then to lyophilization. (cf. Japanese Patent Laid Open Application No. 132,288/1974 published on December 18, 1974).

The pathogenic streptococci include hemolytic Group A streptococci (e.g. *Streptococcus pyogenes* 69882, type A 49; and *Streptococcus pyogenes* T4, type 4), hemolytic Group B streptococci (e.g. *Streptococcus* sp. H36B, type B-I-b; and *Streptococcus pyogenes* B III D 136C, type III), or the like. Any other streptococci which are available from various institutes of microorganisms depositories in the world can be used if they have an esterase-producing capacity without regard to having hemolytic properties or not. The esterases (a) are classified into various serological types such as type A-I, type A-II, type B, type C, etc. in accordance with the kinds of pathogenic streptococci, and these various types of esterase can be all used in the present invention. According to the reagent of the present invention, each anti-esterase antibody (d) corresponding to each type of esterase can separately be determined. For example, when the type A-I esterase (a) is used, the anti-type A-I esterase antibody (d) can be determined, but other anti-esterase antibodies such as anti-type A-II esterase antibody and anti-type B esterase antibody can not be determined. In order to determine the anti-type A-II esterase antibody or anti-type B esterase antibody, type A-II esterase or type B esterase should be used, respectively. This differential determination of each anti-esterase antibody is one of the characteristics of the present invention. It is also possible to determine the total value of two or more kinds of anti-esterase antibodies by using a mixture of two or more types of esterase as the reagent 1.

The protein (b) which is capable of binding to an anti-esterase antibody (d) and is bound to an insoluble carrier, (reagent 2, which may occasionally be referred to as "immuno adsorbent") includes, for example, an antibody against an anti-esterase antibody (d) which is bound to a conventional insoluble carrier such as bacterial cell walls, glass beads or Sephadexes, i.e., hydrophilic, insoluble molecular-sieve chromatographic media, made by cross-linking dextran. The antibody against an anti-esterase antibody (d) may be obtained by administering parenterally the anti-esterase antibody (d) to an animal different from the animal which produced the antibody (d), but preferably is obtained by administering parenterally an immunoglobulin of an animal which produced the antibody (d) to another animal and separating the produced antibody. The antibody against anti-esterase antibody (d) thus obtained is bound to a conventional insoluble carrier (e.g. bacterial cell walls)

with a divalent binding agent (e.g. glutaraldehyde). (cf. Japanese Patent Laid Open Application No. 117,419/1977, published on Oct. 1, 1977).

As the reagent 2, there can be used cell walls of bacteria such as *Staphylococcus aureus* which contain "protein-A". The "protein-A" is a protein that can non-specifically bind to immunoglobulin [cf. Arne Forsgren et al, The Journal of Immunology 97, 822–827 (1966)]. In the bacterial cell walls containing "protein-A", the moiety of "protein-A" corresponds to the protein being capable of binding to the anti-esterase antibody (d) and the remaining moiety corresponds to the insoluble carrier.

The bacterial cell walls containing "protein-A" can be used as they stand, but alternatively, the "protein-A" is isolated and purified and then is bound to an insoluble carrier such as glass beads or Sephadexes. A "protein-A" bound to a Sephadex is commercially available in the name of "Protein-A - Sepharose CL-4B" (manufactured and sold by Pharmacia, Sweden).

The reagent (c) for determining an activity of the esterase (reagent 3) includes all conventional reagents which comprises a substrate for the esterase (a) and a coloring agent which can react with hydrolyzed products of the substrate to give a color, for example a combination of S-acetylthiophenol and 5,5'-dithio-bis(2-nitrobenzoic acid) (hereinafter, referrred to as "DTNB"), a combination of naphthyl acetate and a diazo-compound (e.g. naphthylamine diazonium chloride), nitrophenyl acetate (this compound functions both as a substrate and as a coloring agent), or the like. The reagent 3 may additionally contain other agents such as an enzymatic stopping reagent [e.g. acetone or acidic Tris-malate buffer (pH 5–6)], a buffering agent (e.g. Tris-HCl buffer or phosphate buffer), or the like.

These reagents 1, 2 and 3 are usually in the form of a kit in the liquid or powder state in accordance with the properties of the reagents.

The determination of an anti-esterase antibody (d) in test material by using the reagent of the present invention can be carried out in the following steps.

First step (antigen-antibody reaction)

The reagent 1, i.e. an esterase (a) (antigen), is added to the test material (antibody) and is subjected to an antigen-antibody reaction to give an antigen-antibody complex (e).

Second step (Collection of the antigen-antibody complex)

The antigen-antibody complex (e) is reacted with the reagent 2 (immuno-adsorbent) and the resulting precipitate of the complex (e) is collected.

Third step (Measurement of esterase activity)

The activity of esterase contained in the precipitate obtained in the second step is measured by using the reagent 3.

The first step can usually be carried out by mixing the test material with the esterase (a) (preferably in an excess amount) in a buffer solution (pH 6–8) such as phosphate buffer and incubating the mixture at a temperature of from 20° to 40° C., preferably about 37° C., for 5 to 40 minutes. The resulting mixture containing an antigen-antibody complex (e) is used in the second step.

The second step can usually be carried out by reacting the mixture containing an antigen-antibody complex (e) obtained in the first step with the reagent 2 (immuno-adsorbent) in a buffer solution (pH 6–8) and incubating the mixture at a temperature of from 20° to 40° C., preferably about 37° C., for 5 to 40 minutes, followed by collecting the resulting precipitate by centrifugation or any other conventional separation means.

The third step can usually be carried out by reacting the precipitate obtained in the second step with a substrate for the esterase (a) and then reacting the resultant with a coloring agent, followed by measuring the resulting colored solution in a conventional manner. For example, the precipitate is reacted with S-acetylthiophenol (substrate) and the resulting thiophenol is reacted with DTNB (which is a thiol group-coloring agent), and the resulting yellow color intensity is measured with a colorimeter.

Alternatively, the determination of the anti-esterase antibody (d) can be carried out by exchanging the first step and the second step. That is, the reagent 2 (immuno-adsorbent) is firstly added to the test material in a buffer solution (pH 6–8) and the mixture is reacted likewise, the resulting precipitate collected by a centrifuge is subjected to the antigen-antibody reaction with the reagent 1 and washed by a centrifuge, followed by the measurement of the activity of esterase (the third step).

Further alternatively, the first and second steps can be done simultaneously. That is, the reagent 1 and the reagent 2 are simultaneously added to the test material in a buffer solution (pH 6–8) and the mixture is subjected to the reaction likewise, and the resulting precipitate of antigen-antibody complex is collected and subjected to the measurement of the activity of esterase (the third step). This alternative method is the most convenient because of the simplest procedure. The results of these three methods are well correlated.

The reagent of the present invention is useful for diagnosis of diseases caused by various pathogenic streptococcal infections, particularly hemolytic streptococcal infections.

The present invention is illustrated by the following Examples but is not limited thereto. In the Examples, "%" is % by weight, unless specified otherwise.

EXAMPLE 1

Preparation of esterase (a) (antigen):

A culture medium (pH 7.4, 10 liters) composed of 0.025% of glucose, 0.3% of beef heart infusion, 2% of polypeptone, 0.2% of sodium chloride, 0.2% of dried yeast and 0.4% of disodium hydrogen phosphate was inoculated with *Streptococcus pyogenes* SS 379, type A-40, and the medium was subjected to stationary culture at 37° C. for 16 hours. The resulting culture broth was centrifuged to remove the cells. To the filtrate was added solid ammonium sulfate to give 60% saturation, and the mixture was centrifuged at 6,000×g for 20 minutes. The resulting precipitate was collected and dissolved in a small amount of 0.02M phosphate buffer (pH 7.0), and the mixture was dialyzed against the same buffer solution for 8 hours and lyophilized to give a powder (1.2 g) containing type A-I esterase.

In the same manner as described above, *Streptococcus pyogenes* 69882, type A-49 and *Streptococcus* sp H36B, type B-I-b were cultivated, and there was obtained each powder containing type A-II or type B esterase, respectively.

EXAMPLE 2

Preparation of bacterial cell walls containing "protein-A" (immuno-adsorbent):

A 100 liter fermentor containing a culture medium (pH 7.0, 50 liters) composed of 2% of Bactocasamino acid (manufactured by Difco), 2% of yeast extract, 0.7% of sodium lactate, 2% of sodium glycerophosphate, 0.02% of magnesium sulfate, 0.001% of manganese sulfate, 0.32% of ferric sulfate, 0.32% of sodium citrate, 0.4% of potassium dihydrogen phosphate and 6.25% of disodium hydrogen phosphate was inoculated with *Staphylococcus aureus* Cowan I, and the medium was cultivated for 20 hours at 37° C. (aeration rate, 50 liters/min.; agitation speed, 150 r.p.m.). The resulting culture broth was centrifuged to isolate the cells. The cells thus obtained were suspended in water and were disrupted, and the resulting mixture was washed with 1M aqueous sodium chloride solution (twice) and with water using a centrifuge, and lyophilized to give cell walls containing "protein-A" (58 g).

EXAMPLE 3

Preparation of insoluble antibody (immuno-adsorbent):

An anti-human immunoglobulin rabbit antiserum (50 ml), which was prepared by immunizing rabbit with human immunoglobulin, was diluted with 0.1M potassium phosphate buffer (pH 7.0, 150 ml), and thereto was gradually added a saturated aqueous ammonium sulfate solution (200 ml). The mixture was stirred under ice-cooling for 20 minutes and then centrifuged at 11,000×g for 20 minutes. The resulting precipitate was collected and dissolved in 0.1M potassium phosphate buffer (pH 7.0) to make a total volume of 100 ml. To the solution was gradually added a saturated aqueous ammonium sulfate solution (43 ml), and the mixture was stirred under ice-cooling for 20 minutes and again centrifuged. The supernatant fluid was separated and thereto was gradually added a saturated aqueous ammonium sulfate solution (39 ml), and the mixture was stirred under ice-cooling for 20 minutes and then centrifuged. The resulting precipitate was collected and dissolved in 0.02M potassium phosphate buffer (pH 7.0, 100 ml). The mixture was dialyzed against 0.02M phosphate buffer (pH 7.0, 10 liters) in a dialysis tube overnight. The dialysis was repeated twice.

The dialyzed inner solution was adjusted with the same buffer solution to give a protein concentration of 1 g/50 ml. The resulting mixture was mixed with an aqueous suspension (20 ml) containing cell walls of *Lactobacillus plantarum* ATCC-8014 (1 g, an insoluble carrier) and 1M sodium acetate buffer (pH 5.0, 10 ml). To the mixture was gradually added with stirring 0.8% aqueous glutaraldehyde solution (120 ml) and the mixture was stirred an for additional 2 hours. The reaction mixture was centrifuged at 6,000×g for 10 minutes. The precipitate was collected and suspended in 0.1% bovine serum albumin (BSA) - 0.9% NaCl - 0.04M potassium phosphate buffer (pH 7.0, 500 ml) and subjected to the sonication at 19 KC for 30 seconds, and the resulting mixture was centrifuged. The resulting precipitate was collected and added to the same buffer as used above (100 ml), and the mixture was again sonicated and centrifuged. The procedure was repeated twice, and the resulting precipitate was collected and added to the same BSA-NaCl-potassium phosphate buffer as above (100 ml), and the mixture was sonicated again to give a suspension containing bacterial cell wall-bound immunoglobulin rabbit antibody (an insoluble antibody).

The suspension of an insoluble antibody thus obtained was used for the determination of anti-esterase antibody in the following Examples.

EXAMPLE 4

Determination of anti-type A-I esterase antibody:

reagent 1: A solution (10 ml) which was prepared by dissolving the type A-I esterase (50 mg) obtained in Example 1 in water reagent 2: A suspension (10 ml) which was prepared by suspending the cell walls of *Staphylococcus aureus* Cowan I (750 mg) obtained in Example 2 in water reagent 3-1: 0.3 mM-DTNB-0.05M Tris-HCl buffer (pH 8.0)

reagent 3-2: Substrate solution, 10 mM S-acetylthiophenol in ethanol reagent 3-3: Acetone buffer solution I: 0.02M Phosphate buffer (pH 7.0)
buffer solution II: 0.02M Tris-HCl buffer (pH 8.0)

Sera containing the anti-esterase antibody (d) obtained from patients infected by hemolytic streptococci (two boys of 6 and 4 years old) were used as the test material. The sera were heated at 57° C. for 30 minutes.

Each serum was diluted to 20 fold with buffer solution I, and the diluted serum (0.1 ml) was added to a test tube, and thereto was added Reagent 1 (antigen) (50 μl), and the mixture was incubated at 37° C. for 10 minutes to proceed to antigen-antibody reaction. To the reaction mixture was added reagent 2 (immuno-adsorbent) (0.1 ml), and the mixture was again incubated at 37° C. for 30 minutes. The reaction mixture was washed with buffer solution II twice and centrifuged. The resulting precipitate was collected and suspehded in reagent 3-1 (coloring agent) (1 ml) and thereto was added Reagent 3-2 (substrate) (40 μl), and the mixture was incubated at 37° C. for 30 minutes. After adding reagent 3-3 (enzymatic stopping reagent) (2 ml), the reaction mixture was centrifuged at 1,700×g for 10 minutes. The absorbance of the resulting yellow supernatant fluid was measured at 412 nm in a cell (light path: 1 cm). As a result, the serum from the boy of 6 or 4 years old showed a value of anti-type A-I esterase antibody of 380 or 320, respectively.

The absorbance multiplied by a factor of 1000 was used as the value of antibody (1000×$A_{412}$/5 μl serum/30 min. at 37° C.).

EXAMPLE 5

In the same manner as described in Example 4 except that the type A-II esterase obtained in Example 1 was used as reagent 1 and the insoluble antibody obtained in Example 3 was used as reagent 3, two sera obtained from patients infected by hemolytic streptococci (girl of 7 years old and boy of 4 years old) were assayed. As a result, the sera showed a value of anti-type A-II esterase antibody of 852 and 662, respectively.

EXAMPLE 6

In the same manner as described in Example 4 except that the type B esterase obtained in Example 1 was used as reagent 1, a serum obtained from a patient infected by hemolytic streptococci (girl of 8 years old) was assayed. As a result, the serum showed a value of anti-type B esterase antibody of 924.

EXAMPLE 7

Differential determination of various types of antibody:

In the same manner as described in Example 4 except that either type A-I, type A-II or type B esterase was added as reagent 1, a serum obtained from a patient infected by hemolytic streptococci (girl of 7 years old) and a serum obtained from a non-infected healthy boy (6 years old) were assayed, by which each of three anti-esterase antibodies was differentially measured. The results are shown in Table 1.

TABLE 1

| Test Material | Antibody value | | |
|---|---|---|---|
| | Type A-I | Type A-II | Type B |
| Serum of girl infected by hemolytic streptococci | 970 | 190 | 1250 |
| Serum of non-infected boy | 71 | 55 | 32 |

EXAMPLE 8

Determination of anti-type A-I esterase antibody:

Sera obtained from patients infected by hemolytic streptococci (girl of 5 years old and boy of 6 years old) were used as the test material. The sera were heated at 57° C. for 30 minutes.

Each serum was diluted to 20 fold with buffer solution I as used in Example 4, and the diluted serum (0.1 ml) was added to a test tube, and thereto was added reagent 2 (immuno-adsorbent) (0.1 ml) as used in Example 4, and the mixture was incubated at 37° C. for 30 minutes. The resulting precipitate was collected by centrifugation and washed with buffer solution II as used in Example 4 with a centrifuge. To the resulting precipitate was added Buffer solution I (0.1 ml) as used in Example 4, and the mixture was stirred and thereto was further added reagent 1 (50 μl) as used in Example 4, and the mixture was incubated at 37° C. After 10 minutes, the resulting precipitate was washed with buffer solution II as used in Example 4 with a centrifuge. The activity of esterase in the precipitate was measured in the same manner as in Example 4. As a result, the serum of the girl of 5 years old or the boy of 6 years old showed a value of anti-type A-I esterase antibody of 720 or 430, respectively.

EXAMPLE 9

Determination of anti-type A-I esterase antibody:

A serum obtained from a boy (5 years old) infected by hemolytic streptococci was heated at 57° C. for 30 minutes. The serum was diluted to 20 fold with buffer solution I as used in Example 4. The diluted serum (0.1 ml) was added to a test tube, and thereto was added reagent 1 (50 μl) as used in Example 4 and reagent 2 (0.1 ml) as used in Example 4, and the mixture was incubated at 37° C. for 10 minutes. The resulting precipitate was treated in the same manner as described in Example 4, and the antibody value was measured likewise. As a result, the serum showed an antibody value of 475.

EXAMPLE 10

Comparison of the methods in Examples 4, 8 and 9:

With respect to several sera obtained from several children patients infected by hemolytic streptococci as mentioned in Table 2, the anti-type A-I esterase antibody was measured in the same manner as described in Examples 4, 8 and 9, respectively. The results are shown in Table 2.

TABLE 2

| Test material | Method for measurement | | |
|---|---|---|---|
| | Example 4 | Example 8 | Example 9 |
| Serum of girl of 4 years old | 100.0 | 89.9 | 92.0 |
| Serum of girl of 5 years old | 100.0 | 92.3 | 90.9 |
| Serum of boy of 5 years old | 100.0 | 87.5 | 93.7 |
| Serum of boy of 4 years old | 100.0 | 98.2 | 88.5 |
| Serum of girl of 6 years old | 100.0 | 90.5 | 95.2 |

[Remark]:
The value in the above table shows the relative antibody value when the value in Example 4 is shown as 100.

EXAMPLE 11

Determination of anti-type A-I esterase antibody:

The serum obtained from a girl (8 years old) as used in Example 7 was diluted 2 fold successively with buffer solution I as used in Example 4, and values of the anti-type A-I esterase antibody were determined in the same manner as described in Example 4. As shown in Table 3, there was a linear relationship between the antibody values and dilution folds.

TABLE 3

| Degree of dilution | 1/16 | 1/8 | 1/4 | 1/2 | 1/1 |
|---|---|---|---|---|---|
| Antibody value | 58 | 121 | 245 | 487 | 975 |

EXAMPLE 12

Correlation between the value of anti-type A-I esterase antibody and ASO value:

With respect to sera obtained from 102 child patients infected by hemolytic streptococci, the value of anti-type A-I esterase antibody was determined in the same manner as described in Example 4 and the data were compared with the value of an antibody against Streptolysin O (ASO value) determined by the method of Rantz-Randall [cf. Proc. Soc. Exp. Biol. Med., 59, 22 (1945)]. The correlation of both data is shown in the accompanying FIG. 1.

What is claimed is:

1. A reagent kit for the quantitative determination of an antibody against an esterase from pathogenic streptococci in human blood serum, comprising:
    (a) a predetermined quantity of an esterase from pathogenic streptococci, said predetermined quantity being at least immunochemically equivalent to the quantity of said antibody to be determined;
    (b) a predetermined quantity of a protein-A, said protein-A being able to bind non-specifically to said antibody to be determined and being bound to an insoluble carrier, said predetermined quantity being at least immunochemically equivalent to the quantity of said antibody to be determined; and
    (c) a predetermined quantity of a substrate reagent that measures esterase activity, which is selected from the group consisting of S-acetylthiophenol, naphthylacetate and nitrophenylacetate, and said predetermined quantity being sufficient to measure quantitatively the esterase in an esterase-anti-esterase antibody-insoluble protein-A complex.

2. The reagent kit of claim 1, wherein said esterase is selected from the group consisting of a type A-I esterase, a type A-II esterase, the type B esterase, and a mixture thereof.

3. The reagent kit of claim 1, wherein said insoluble carrier is selected from the group consisting of bacterial cell walls, glass beads, and a hydrophilic, insoluble molecular-sieve chromatographic medium, made by cross-linking dextran.

4. The reagent kit of claim 1, wherein said protein-A bound to an insoluble carrier is bacterial cell walls containing a protein-A.

5. A method for the quantitative determination of an antibody against an esterase from pathogenic streptococci in human blood serum comprising:
   (a) adding at least an immunochemical euqivalent of an esterase from pathogenic streptococci to human blood serum containing said antibody to be determined;
   (b) adding to the mixture of step (a) at least an immunochemical equivalent of a protein-A, said protein-A being able to bind non-specifically to said antibody to be determined and being bound to an insoluble carrier to form an esterase-anti-esterase antibody-insoluble protein-A complex;
   (c) separating said complex from the mixture of step (b) by centrifugation; and
   (d) mesuring the activity of the esterase in said complex by using a substrate which is selected from the group consisting of S-acethylthiophenol, naphthylacetate and nitrophenlacetate.

6. A method for the quantitative determination of an antibody against an esterase from pathogenic streptococci in human blood serum comprising:
   (a) adding at least an immunochemical euqivalent of a protein-A, said protein-A being able to bind non-specifically to said antibody to be determined and being bound to an insoluble carrier to human blood serum containing said antibody to be determined;
   (b) adding to the mixture of step (a) at least an immunochemical equivalent of an esterase from pathogenic streptococci to form an esterase-anti-esterase antibody-insoluble protein-A complex;
   (c) separating said complex from the mixture of step (b) by centrifugation; and
   (d) measuring the activity of the esterase in said complex by using a substrate which is selected from the group consisting of S-acethylthiophenol, naphthylacetate and nitrophenylacetate.

7. A method for the quantitative determination of an antibody against an esterase from pathogenic streptococci in human blood comprising:
   (a) adding simultaneously at least an immunochemical equivalent of an esterase from pathogenic streptococci and at least an immunochemical equivalent of a protein-A, said protein-A being able to bind non-specifically to said antibody to be determined and being bound to an insoluble carrier to human blood serum containing said antibody to be determined to form an esterase-anti-esterase antibody-insoluble protein-A complex;
   (b) separating said complex from the mixture of step (a) by centrifugation; and
   (c) measuring the activity of the esterase in said complex by using a substrate which is selected from S-acetylthiophenol, naphthylacetate and nitrophenylacetate.

* * * * *